(12) United States Patent
Ohashi et al.

(10) Patent No.: US 6,299,871 B1
(45) Date of Patent: Oct. 9, 2001

(54) ORALLY-ADMINISTRABLE THERAPEUTIC AND/OR PROPHYLACTIC AGENT FOR HTLV-1-RELATED DISEASES

(75) Inventors: Kunihiro Ohashi; Masashi Kurimoto, both of Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 09/357,913

(22) Filed: Jul. 21, 1999

(30) Foreign Application Priority Data

Jul. 24, 1998 (JP) .................................................. 10-209294

(51) Int. Cl.[7] .................................................. A61K 37/66
(52) U.S. Cl. ...................... 424/85.5; 424/85.1; 424/85.4; 435/69.51
(58) Field of Search .................................. 424/85.1, 85.4, 424/85.5; 435/69.51

(56) References Cited

U.S. PATENT DOCUMENTS 5,824,300 * 10/1998 Cummins ............................ 424/85.7

OTHER PUBLICATIONS

Ishihara, K., *Skin Cancer*, vol. 12, No. 2 (11/1997), pp. 301–314.

* cited by examiner

*Primary Examiner*—Jeffrey Stucker
(74) *Attorney, Agent, or Firm*—Browdy and Neimark

(57) ABSTRACT

Disclosed are an orally-administrable therapeutic and/or prophylactic agent for HTLV-1-related diseases, which comprises an interferon-γ as an effective ingredient and a pharmaceutically-acceptable carrier, and a method for treating and/or preventing the diseases with the agent. The HTLV-1-related diseases include ATL, rheumatoid arthritis, Sjögren's syndrome, SLE, uveitis, and immunopathies.

12 Claims, No Drawings

ORALLY-ADMINISTRABLE THERAPEUTIC AND/OR PROPHYLACTIC AGENT FOR HTLV-1-RELATED DISEASES

BACKGROUND OF THE INVENTION

1. Field of the Invention

The present invention relates to an orally-administrable therapeutic and/or prophylactic agent for HTLV-1 (Human T-cell Lymphotropic Virus Type 1) related diseases, and more particularly to an orally-administrable therapeutic and/or prophylactic agent for HTLV-1-related diseases, which comprises an interferon-γ (abbreviated as IFN-γ hereinafter) as an effective ingredient.

2. Description of the Prior Art

Adult T-cell leukemia (abbreviated as ATL hereinafter) is a T-cell leukemia with characteristic symptoms, found and reported by Cache TAKATSUKI in 1976. The disease is an intractable and district-specific disease, and in some cases it may cause a malignant lymphoma-like symptom; In Japan, there found many patients in the South and East Japan including Kyushu-, Okinawa- and Shikoku-Islands. In overseas, in the tropical regions such as the Caribbean Sea and the South India. Most of the leukemia cells induced by ATL have CD4-positive and CD8-negative helper T-cell surface antigens, and show a specific change in nuclear. It was revealed that ATL is induced by HTLV-1, a C-type retrovirus, as a causative virus thereof.

Epidemiological research revealed that HTLV-1-infected patients or HTLV-1 carriers may cause not only ATL but induce malignant tumors at a relatively-high efficiency, as well as neuropathies and immunopathies called HAM (HTLV-1-associated myelopathy). HTLV-1 is now being researched on that, in addition to ATL, it correlates to another diseases. Furthermore, it is pointed out that HTLV-1 may relate to chronic rheumatoid arthritis, Sjögren syndrome, systemic lupus erythematosus (SLE), uveitis, etc.

HTLV-1 infection can be easily diagnosed by detecting an HTLV-specific antibody in blood and by confirming the presence of an HTLV-1 proviral DNA. Symptoms and developments of HTLV-1-infected patients are varied, and the patients may become to show the symptoms at their age of 50th. Physiologically, there observed the downfall of myelin sheathes and the loss of axons from the upper part of cervicals through lumbars, the invasion of mononuclear cells such as lymphocytes and macrophages, the proliferation of astrogrias, and a slight level of the mononuclear cells' invasion in the part of brain stem and the substantia alba of cerebrum and cerebellum.

The percentage of the incidence of ATL induced by HTLV-1 is relatively low. However, once occurred, the symptom of the patients infected with the virus is rapidly worsened, and the treatment is quite difficult. Conventional therapies include the administration of a relatively-large amount of adrenal cortical hormone, and chemical- and radio-therapies in accordance with those for malignant tumors. They are, however, merely temporal symptomatic therapies which are far from intrinsic therapy. As another clinical-test-treatment for ATL as an HTLV-1-related disease, Kazuyuki ISHIHARA proposed in *Skin Cancer*, Vol. 12, No. 2, pp. 301–314 (1997) an intramuscular injection of IFN-γ, where several millions units of IFN-γ are injected to a patient daily for over eight weeks. In such a treatment, patients are forced to stay in hospitals or allowed to go to hospitals frequently, resulting in physical- and mental-pains and economical burdens. In the latter case, when patients unexpectedly could not go to hospitals on their prescribed administration dates, the medicinal administration control is not sufficiently conducted, and as a drawback, this hinders the expected therapeutic effect. Although IFN-γ is per se a safer medicine which scarcely induces side effects even when administered to patients at a relatively-high dose, the above daily high-dose as much as several hundreds units of IFN-γ may result in side effects such as serious depression of liver function, leukopenia, neutropenia, calcium lowering, and fervescence. In the most serious case, the administration must be ceased.

Under these backgrounds, greatly expected is the establishment of a relatively-safe medicine which can intrinsically and effectively treat and/or prevent HTLV-1-related diseases, and lower the patients' mental, physical, and economical burdens.

SUMMARY OF THE INVENTION

The present invention aims to provide a medicament with lesser side effects, which can intrinsically and effectively treat and/or prevent HTLV-1-related diseases.

The present inventors energetically researched on medicaments which can intrinsically and effectively treat and/or prevent HTLV-1-related diseases, and on the administration route. As a result, they solved the above object by establishing an orally-administrable therapeutic and/or prophylactic agent for HTLV-1-related diseases, which comprises an IFN-γ as an effective ingredient. As a characteristic feature of the present invention, the oral administration of IFN-γ as an effective ingredient more effectively treats and/or prevents HTLV-1-related diseases at an extremely-lower dose than another administrations.

DETAILED DESCRIPTION OF THE INVENTION

Explaining the preferred embodiments of the present invention, the IFN-γ, which is incorporated as an effective ingredient into the present orally-administrable therapeutic and/or prophylactic agent for HTLV-1-related diseases, includes natural IFN-γs produced from IFN-γ-producing human leukocytes and established cell lines, and recombinant IFN-γs obtained by introducing genes for encoding the above IFN-γs into animal cells or microorganisms such as the species *Escherichia coli* to transform them by the recombinant DNA technology. These IFN-γs arbitrarily used in the present invention include not only those in a highly-purified form having a specific activity of at least $1 \times 10^7$ units/mg protein but those in a crude form which contain merely pharmaceutically-acceptable impurities as long as they attain the present object. Because the present agent is orally administrable, it does not necessarily require the highest possible purity of IFN-γ requisite for intramuscular- and intravenous-injections, and it can be arbitrarily prepared even with a relatively-low purity IFN-γ. Using these IFN-γs, the present orally-administrable agent can be prepared at a relatively-low cost. In the present invention, two or more types of IFN-γs can be used as the IFN-γs. With a viewpoint of antigenicity, human IFN-γs, in particular, natural types of IFN-γs, can be more advantageously used.

Into the present orally-administrable agent can be arbitrarily incorporated one or more pharmaceutically-acceptable diluents, excipients, fillers, stabilizers, pH-controlling agents, biologically-active substances, etc., in addition to the IFN-γ as an effective ingredient.

The stabilizers used in the present invention mean agents capable of stabilizing the IFN-γ; saccharides and sugar alcohols such as glucose, galactose, xylose, fructose, sucrose, maltose, trehalose, neotrehalose, isotrehalose, sorbitol, mannitol, maltitol, lactitol, lactosucrose, maltooligo-saccharides, and polysaccharides; cyclodextrins, hydroxyethyl starches, dextrins, and dextrans; salts such as sodium glucronate, phosphates, and metal salts; and serum albumin, gelatin, amino acids, and non-ionic surfactants. Among these stabilizers, maltose and trehalose stably retain the present effective ingredient(s) for a relatively-long period of time.

Except for the non-ionic surfactants, the percentage of the above stabilizers which are incorporated into the present orally-administrable agent is not specifically restricted; Generally, it is in the range of about 0.01 to below 100 w/w %, preferably, about 0.1 to below 100 w/w %, and more preferably about 1 to below 100 w/w %, based on the weight of the present orally-administrable agent. The percentage of the non-ionic surfactants is from one microgram to one milligram, and preferably 10 micrograms to one milligram per gram of the present orally-administrable agent. Depending on the form of the present orally-administrable agent, the addition of the stabilizers in an amount within the above range stably retains the activities of the IFN-γ for, in general, at least 36 months at 4° C. conditions, and for at least six months even at ambient temperature. In the case of using maltose and/or trehalose as the stabilizers, the IFN-γ can be usually retained stably for at least 12 months even at ambient temperature. While the other stabilizers tend to have an inferior stabilizing-activity to that attained by maltose and/or trehalose.

The content of the IFN-γ, which is incorporated as an effective ingredient into the present orally-administrable agent, is an amount sufficient for effectively reducing the HTLV-1 virus level and its antibody level. Usually, it is from about 0.1 to about $10^9$ units; preferably, from about one to about $10^7$ units; more preferably, from about 10 to about $10^5$ units; and most preferably from about $10^2$ to about $10^4$ units per gram of the present orally-administrable agent. When the present agent is in a dose unit form, it should preferably contain an about 0.1 to about $10^6$ units, preferably, about 10 to about $10^5$ units of the IFN-γ.

The form of the present orally-administrable agent is selected from those in orally-administrable forms of liquids, pastes, troches, capsules, powders, granules, tablets, and enteric coated agents. In the case of formulating the present orally-administrable agent into a liquid or paste form, the agent thus obtained is adjusted to a pH that does not inactivate the IFN-γ as the present effective ingredient, i.e., pHs of from about 4 to about 9, and preferably pHs of 6–8. The present orally-administrable agent should preferably be stored at 4° C. under dark conditions to stably keep the activity and quality, independently of its form and shape. Since the IFN-γ is unstable under strong-acid conditions, the present orally-administrable agent should preferably be formulated into a granule, sugar-coated agent, capsule or enteric-coated agent to prevent the effective ingredients from being inactivated by gastric acid after orally administered. Particularly, the present orally-administrable agent in the form of an enteric-coated agent is most preferable. The processing method for formulating the present orally-administrable agent into various shapes and forms should not be restricted, and it can be appropriately selected from conventional ones.

Explaining the dose of the present orally-administrable therapeutic and/or prophylactic agent for HTLV-1-related diseases, in case of the present agent containing the IFN-γ as an effective ingredient, the oral dose of IFN-γ is one to $1\times10^4$ units/adult/day/kg of the body weight; preferably, $1\times10$ to $1\times10^4$ units/adult/day/kg of the body weight; and more preferably, $1\times10^2$ to $1\times10^3$ units/adult/day/kg of the body weight, at 1–4 shots/day or 1–7 shots/week over one week to one year. In the case of the present orally-administrable agent, which comprises the IFN-γ is in a unit dose form, the effective ingredients are administered to subjects within the above dose range. The administration period is not specifically restricted and can be arbitrarily set depending on the types, contents and doses of the effective ingredients, and patients' symptoms; usually, 1–24 months, preferably, 3–18 months, and more preferably, 6–12 months.

The following Experiments and Examples describe the present invention in more detail:

EXPERIMENT 1

Treatment of Adult T-cell Leukemia

Eight HTLV-1 carriers, who were infected with HTLV-1 but not yet showed the symptoms, were divided into Groups A, B and C consisting of three, three and two subjects, respectively. The subjects of Group A were administered with the present orally-administrable agent, 200 mg per tablet, containing 1,000 units of IFN-γ, obtained by the later described method in Example 1, while the subjects of Group B were administered with another type of the present orally-administrable agent, 200 mg per tablet, containing 10,000 units of IFN-γ, obtained by the later described method in Example 2, at a dose of 3 shots/day/subject over 12 months. The subjects of Group C were orally administered similarly as above with an orally-administrable agent, 200 mg per tablet, free of IFN-γ and consisting of a base. Every patient was sampled their blood before the administration tests and sampled at 3rd, 6th, 9th and 12th months after initiation of the tests to determine the virus level of HTLV-1 and the level of antibody against HTLV-1. The levels of the virus and antibody were respectively determined by conventional hybridization method and EIA method (enzyme immunosolvent assay). The virus level was expressed with a relative value (%) based on the level before the administration test being regarded as 100%. The antibody level was expressed with the symbols "++", "+" and "−" which meant "high", "low", and "below the detectable level", respectively. The results are in Table 1.

TABLE 1

| Group | | | Before administration | After administration | | | |
|---|---|---|---|---|---|---|---|
| | | | | 3rd month | 6th month | 9th month | 12th month |
| A (Present invention) | No. 1 | Virus level | 100% | 100% | 80% | 30% | 10% |
| | | Antibody level | ++ | ++ | ++ | ++ | ++ |
| | No. 2 | Virus level | 100% | 80% | 1% | 0.01% | 0% |
| | | Antibody level | ++ | ++ | ++ | + | − |

TABLE 1-continued

| Group | | | Before administration | After administration | | | |
|---|---|---|---|---|---|---|---|
| | | | | 3rd month | 6th month | 9th month | 12th month |
| | No. 3 | Virus level | 100% | 60% | 0.5% | 0.1% | 0.01% |
| | | Antibody level | ++ | ++ | ++ | ++ | + |
| B | No. 1 | Virus level | 100% | 15% | 0.01% | 0% | 0% |
| (Present invention) | | Antibody level | ++ | ++ | ++ | + | − |
| | No. 2 | Virus level | 100% | 20% | 0.01% | 0% | 0% |
| | | Antibody level | ++ | ++ | ++ | + | − |
| | No. 3 | Virus level | 100% | 50% | 3% | 0.01% | 0% |
| | | Antibody level | ++ | ++ | ++ | + | − |
| C | No. 1 | Virus level | 100% | 100% | 100% | 102% | 105% |
| (Control) | | Antibody level | ++ | ++ | ++ | ++ | ++ |
| | No. 2 | Virus level | 100% | 100% | 100% | 101% | 102% |
| | | Antibody level | ++ | ++ | ++ | ++ | ++ |

In Groups A and B administered with the present orally-administrable agent of IFN-γ, the HTLV-1 virus level was lowered depending on the IFN-γ concentration. In particular, after the administration tests, no HTLV-1 was detected in the subjects of Group A, No. 2, and of Group B, Nos. 1 and 2, and no HTLV-1 was detected in them even six months after the tests. The data strongly indicates that HTLV-1 was completely eliminated from these subjects. In Groups A and B, there found some subjects who lowered leukocytes in number which might be caused by IFN-γ, but after the oral-administration test all of them recovered to their normal levels within a relatively-short period of time. In the groups with IFN-γ, no subject complained about side effects such as fervescence, languor, and lack of appetite.

These results indicate the effectiveness and safety of the present orally-administrable therapeutic and/or prophylactic agent for HTLV-1-related diseases.

EXPERIMENT 2

Treatment of Adult T-cell Leukemia

Three patients, who were suffering from adult T-cell leukemia and found out with skin erythema characteristic of ATL, were orally administered with an orally-administrable agent, 200 mg per tablet, according to the present invention, which contained 1,000 units of the later described IFN-γ obtained in Example 1, at a dose of thrice-a-day for six months. As a control, two patients, who were observed with skin erythema characteristic of ATL, were orally administered with an orally-administrable agent, 200 mg per tablet, free of IFN-γ and consisting of a base, prepared according to the method in Example 1. Every patient was macroscopically observed his or her skin erythema before initiating the administration, and at 2nd and 4th months and 6th month (completion of the administration) after the administration, and examined for HTLV-1 virus level in blood, level of antibody against HTLV-1, leukocyte number, and percentage (%) of abnormal lymphocytes to normal ones. The patients were asked for examining side effects such as fervescence, languor, and lack of appetite. The assay for virus and antibody levels, and the evaluation of the antibody level were conducted similarly as in Experiment 1. The evaluation of the degree of skin erythema was expressed with the symbols "++", "+" and "−" which meant that the levels or symptoms of skin erythema were "high", "low", and "diminished", respectively. The results are in Table 2.

TABLE 2

| Test No. | | | Before administration | After administration | | |
|---|---|---|---|---|---|---|
| | | | | 2nd month | 4th month | 6th month |
| No. 1 | Virus level | | 100% | 100% | 100% | 100% |
| (Present invention) | Antibody level | | ++ | ++ | ++ | ++ |
| | Skin erythema level | | ++ | ++ | + | − |
| | Hemateikon | leukocyte (cells/mm$^3$) | 11000 | 11000 | 10000 | 10000 |
| | | Abnormal lymphocyte (%) | 5.3% | 5.2% | 4.5% | 2.3% |
| | Side effects | Fervescence | Non | Non | Non | Non |
| | | Languor | Non | Non | Non | Non |
| | | Lack of appetite | Non | Non | Non | Non |
| No. 2 | Virus level | | 100% | 60% | 0.5% | 0.1% |
| (Present invention) | Antibody level | | ++ | ++ | ++ | ++ |
| | Skin erythema level | | ++ | ++ | ++ | + |
| | Hemateikon | leukocyte (cells/mm$^3$) | 12500 | 12000 | 12000 | 11500 |
| | | Abnormal lymphocyte (%) | 5.8% | 5.5% | 5.4% | 5.2% |
| | Side effects | Fervescence | Non | Non | Non | Non |
| | | Languor | Non | Non | Non | Non |
| | | Lack of appetite | Non | Non | Non | Non |
| No. 3 | Virus level | | 100% | 80% | 1% | 0.01% |
| (Present invention) | Antibody level | | ++ | + | − | − |

TABLE 2-continued

| Test No. | | | Before administration | After administration | | |
|---|---|---|---|---|---|---|
| | | | | 2nd month | 4th month | 6th month |
| | Skin erythema level | | ++ | + | + | − |
| | Hemateikon | leukocyte (cells/mm$^3$) | 12000 | 12000 | 12000 | 11500 |
| | | Abnormal lymphocyte (%) | 6.8% | 6.5% | 6.4% | 6.2% |
| | Side effects | Fervescence | Non | Non | Non | Non |
| | | Languor | Non | Non | Non | Non |
| | | Lack of appetite | Non | Non | Non | Non |
| No. 4 (Control) | Virus level | | 100% | 101% | 102% | 102% |
| | Antibody level | | ++ | ++ | ++ | ++ |
| | Skin erythema level | | ++ | + | + | − |
| | Hemateikon | leukocyte (cells/mm$^3$) | 11500 | 11500 | 11200 | 11000 |
| | | Abnormal lymphocyte (%) | 5.5% | 5.9% | 5.9% | 6.0% |
| | Side effects | Fervescence | Non | Non | Non | Non |
| | | Languor | Non | Non | Non | Non |
| | | Lack of appetite | Non | Non | Non | Non |
| No. 5 (Control) | Virus level | | 100% | 102% | 103% | 104% |
| | Antibody level | | ++ | ++ | ++ | ++ |
| | Skin erythema level | | ++ | ++ | ++ | ++ |
| | Hemateikon | leukocyte (cells/mm$^3$) | 12000 | 12200 | 12100 | 12000 |
| | | Abnormal lymphocyte (%) | 5.0% | 5.2% | 5.4% | 5.6% |
| | Side effects | Fervescence | Non | Non | Non | Non |
| | | Languor | Non | Non | Non | Non |
| | | Lack of appetite | Non | Non | Non | Non |

As shown in Table 2, depending on the administration period of IFN-γ, the patients in the groups with the present orally-administrable agent were lowered or reduced in the level of HTLV-1 virus, antibody, skin erythema, and abnormal lymphocyte. These patients were slightly lowered in leukocyte number which might be induced by IFN-γ, but after completion of the IFN-γ administration they all recovered their normal leukocyte levels within a relatively-short period of time. In the group with the orally-administrable agent of IFN-γ, no patient complained about side effects such as fervescence, languor, and lack of appetite.

These results show the effectiveness and safety of the present orally-administrable therapeutic and/or prophylactic agent for HTLV-1-related diseases.

EXPERIMENT 3

Treatment of Sjögren's Syndrome

Eight patients with Sjögren's syndrome were divided into two groups which consisted of four subjects each. Patients in one group were orally administered with the present orally-administrable agent, 200 mg per tablet, containing 1,000 units of IFN-γ obtained by the later described method in Example 1, at a dose of thrice-a-day over six months, while those in another group were orally administered with an orally-administrable agent, 200 mg per tablet, free of IFN-γ and consisting of a base, prepared similarly as above. With an index of the lowering of salivary secretion characteristic of patients with the syndrome, the secretion volume before and after the administration was measured by the Saxon method to evaluate the affectivity of the present agent. The results are in Table 3.

TABLE 3

| | Salivary secretion (g/min) | |
|---|---|---|
| | Present invention (Group with IFN-γ) | Control (Group with no IFN-γ) |
| Before administration | 0.62 ± 0.43 | 0.56 ± 0.34 |
| After administration | 1.23 ± 0.65 | 0.45 ± 0.38 |

As evident from the results in Table 3, the patients of the group with the present IFN-γ orally-administrable agent significantly increased in salivary secretion. In the control, no increment of salivary secretion was found.

The data indicates that the present orally-administrable therapeutic and/or prophylactic agent for HTLV-1-related diseases is strongly effective on Sjögren's syndrome.

EXPERIMENT 4

Immuno-activating Activity

Four healthy volunteers, consisting of two males and females each, were divided into two groups consisting of both sexes. The subjects, Nos. 1 and 2, in one group were orally administered with, as the present agent, an orally-administrable agent, 200 mg per tablet, containing 100 units of an IFN-γ prepared in accordance with the later described method in Example 1, at a dose of thrice-a-day over six months. The subjects, Nos. 3 and 4, in another group were orally administered with an orally-administrable agent, 200 mg per tablet, free of IFN-γ and consisting of a base, which had been prepared similarly as above agent. The patients in each group were sampled their blood before and two-weeks after the administration for assaying NK-cell activity and tumor-cell-killing activity of mononuclear cells.

The NK cell activity was assayed by separating lymphocytes from a sampled blood, and evaluating the activity based on the cytotoxic effect by the lymphocytes against K-562 cell, ATCC CCL 243, human chronic myelogenous leukemia; Peripheral lymphocytes as effector cells and $^{51}$Cr-labeled K-562 cells as target cells were mixed at different ratios of effector cell/target cell (E/T ratio) and cultured for four hours, followed by measuring the radio-activity of $^{51}$Cr released in the supernatant. The results are in Table 4. The increment of the radio-activity means that the present orally-administrable agent activated NK cells as immunocompetent cells.

TABLE 4

| Volunteer No. | Present invention (Group with IFN-γ) | | Control (Group with no IFN-γ) | |
| --- | --- | --- | --- | --- |
| | No. 1 | No. 2 | No. 3 | No. 4 |
| Radioactivity | | | | |
| Before administration | 18.4 | 26.5 | 16.3 | 20.3 |
| After administration | 24.4 | 30.4 | 17.4 | 19.7 |

As evident from the results in Table 4, in the control, there found no increment of NK cell activity but found a remarkable increment in the group with the present orally-administrable therapeutic and/or prophylactic agent for HTLV-1-related diseases.

The cell-killing activity by mononuclear cells was measured by separating mononuclear cells from the volunteers' blood, and evaluating the activity based on the cytotoxic reaction against A375.S2, ATCC CRL-1872, human malignant melanoma; It was measured by mixing the mononuclear cells as effector cells and [$^{125}$I]uridine-labeled A375.S2 cells as target cells in a ratio of effector cells to target cells (E/T ratio) of 20, incubating the cells for 72 hours, and measuring the radio-activity of the remaining target cells for determining the cell-killing activity of the mononuclear cells. The results are in Table 5. The increment of radio-activity means that the present orally-administrable agent activated the cell killing activity by mononuclear cells as immunocompetent cells.

TABLE 5

| Volunteer No. | Present invention (Group with IFN-γ) | | Control (Group with no IFN-γ) | |
| --- | --- | --- | --- | --- |
| | No. 1 | No. 2 | No. 3 | No. 4 |
| Radioactivity | | | | |
| Before administration | 1.2 | 2.4 | 2.3 | 1.3 |
| After administration | 3.4 | 5.3 | 2.1 | 1.2 |

As evident from the results in Table 5, in the control, there found no increment of cell killing activity by human mononuclear cells but found a remarkable increment in the group with the present orally-administrable therapeutic and/or prophylactic agent for HTLV-1-related diseases.

The following Examples describe the preferred embodiments according to the present invention in more detail:

EXAMPLE 1

Orally-administrable Agent

A natural human IFN-γ having a specific activity of about $1 \times 10^7$ units/mg protein commercialized by Hayashibara Biochemical Laboratories, Inc., Okayama, Japan, and "TREHAOSE®", a trehalose commercialized by Hayashibara Shoji, Inc., Okayama, Japan, were mixed, and the mixture was tabletted in a usual manner into a crude tablet, 180 mg, containing $1 \times 10^3$ units of IFN-γ. A base for enteric coating, consisting of 100 g hydroxypropylmethylcellulose phthalate (HPMCP), 500 ml ethanol, and 100 of refined water, was prepared. The above crude tablet was coated with the base into an enteric coated tablet, 200 mg, as the present orally-administrable agent.

Since the product has, as an effective ingredient, an IFN-γ stabilized by trehalose and is enteric coated, the decomposition of IFN-γ by gastric acid is well prevented. The product can be arbitrarily used in the treatment and/or the prevention of ATL, rheumatoid arthritis, Sjögren's syndrome, SLE, uveitis, and immunopathies. Especially, ATL can be effectively treated with the product.

EXAMPLE 2

Orally-administrable Agent

A natural human IFN-γ having a specific activity of about $1 \times 10^7$ units/mg protein commercialized by Hayashibara Biochemical Laboratories, Inc., Okayama, Japan; "FINETOSE®", a crystalline maltose anhydride commercialized by Hayashibara Shoji, Inc., Okayama, Japan; and "TREHAOSE®", a trehalose commercialized by Hayashibara Shoji, Inc., Okayama, Japan, were mixed, and the mixture was tabletted in a usual manner into a crude tablet, 170 mg, containing $1 \times 10^4$ units of IFN-γ. A base for enteric coating, consisting of 200 g acetic acid cellulose phthalate (CPA), 500 ml ethanol, and 100 of refined water, was prepared. The above crude tablet was coated with the base into an enteric coated tablet, 200 mg, as the present orally-administrable agent.

Since the product has, as an effective ingredient, an IFN-γ stabilized by maltose and trehalose and is enteric coated, the decomposition of IFN-γ by gastric juice is well prevented. The product can be arbitrarily used in the treatment and/or the prevention of ATL, rheumatoid arthritis, Sjögren's syndrome, SLE, uveitis, and immunopathies. Especially, ATL can be effectively treated with the product.

EXAMPLE 3

Orally-administrable Agent

In 1,000 ml (pH 7.0) of a physiological saline containing both 100 µg/ml human serum albumin and 10 w/v % maltose was dissolved 5,000 units of a recombinant human IFN-γ with a specific activity of about $1 \times 10^6$ units/mg protein, commercialized by Japan Chemical Research, Tokyo, Japan. The resulting solution was in a usual manner filtered with a membrane filter to obtain an orally-administrable agent as the present orally-administrable agent. The dose of the product is in the range of 10–100 ml/shot.

Since the product is stabilized by maltose, i.e., the IFN-γ as an effective ingredient is stably retained over a period of 36 months under 4° C. conditions, it can be arbitrarily used in the treatment and/or the prevention of ATL, rheumatoid arthritis, Sjögren's syndrome, SLE, uveitis, and immunopathies. Especially, ATL can be effectively treated with the product.

EXAMPLE 5

Orally-administrable Agent

A physiological saline containing 5 w/v % "FINETOSE®", a crystalline maltose anhydride commercialized by Hayashibara Shoji, Inc., Okayama, Japan; 5 w/v % "TREHAOSE®", a trehalose commercialized by Hayashibara Shoji, Inc., Okayama, Japan; and one w/v % gelatin was prepared and allowed to dissolve a natural human IFN-γ with a specific activity of about $1 \times 10^7$ units/mg protein to give a concentration of 10 units/ml of IFN-γ. The solution was in a usual manner filtered with a membrane filter for sterilization to obtain an orally-administrable agent as the present orally-administrable agent. The dose of the product is in the range of 10–50 ml/shot. Since the product is stabilized by maltose and trehalose where the IFN-γ as an effective ingredient is stably retained over a period of 36 months under 4° C. conditions, it can be arbitrarily used in the treatment and/or the prevention of ATL, rheumatoid arthritis, Sjögren's syndrome, SLE, uveitis, and immunopathies. Especially, ATL can be effectively treated with the product.

As described above, the present invention was made based on the finding that, when orally administered to patients with HTLV-1-related diseases, IFN-γ effectively treats and/or prevents ATL, rheumatoid arthritis, Sjögren's syndrome, SLE, uveitis, and immunopathies within a relatively-short period of time. The present orally-administrable agent intrinsically treats and/or prevents HTLV-1-related diseases which have been deemed substantially impossible of the treatment and/or the prevention with conventional adrenocorticotropic hormones, and chemical- and radio-therapies. The present agent most effectively acts on HTLV-1-related diseases, particularly, ATL, and can completely eliminate the virus from the body of HTLV-1-carriers.

The present invention with such outstanding effects will greatly contribute to this art.

While there has been described what is at present considered to be the preferred embodiments of the invention, it will be understood the various modifications may be made therein, and it is intended to cover the appended claims all such modifications as fall within the true spirits and scope of the invention.

We claim:

1. An orally-administrable therapeutic and/or prophylactic agent for HTLV-1-related diseases induced by HTLV-1 (human T-cell lymphotropic virus type 1), which comprises an effective ingredient consisting of interferon-γ and a pharmaceutically-acceptable carrier, and which does not contain interferon-α.

2. The agent of claim 1, wherein said interferon-γ is of a natural origin or one obtained by the recombinant DNA technology.

3. The agent of claim 1, which further comprises, as a stabilizer for said interferon-γ, one or more members selected from the group consisting of saccharides, salts, amino acids, serum albumins, gelatin, non-ionic surfactants, glucuronic acid, dextrans, and hydroxyethyl starches.

4. The agent of claim 1, which contains about 0.1 to about $10^6$ units of said interferon-γ.

5. The agent of claim 1, which is in the form of a granule, sugar-coated agent, troche or enteric-coated agent.

6. The agent of claim 1, wherein said HTLV-1-related diseases are adult T-cell leukemia (ATL), Sjögren syndrome, chronic rheumatoid arthritis, systemic lupus erythematosus (SLE), uveitis, and immunopathies.

7. The agent of claim 1, which contains about 10 to about $10^5$ units of IFN-γ per gram of the agent.

8. The agent of claim 1, which is in a dose unit form and which contains an about 0.1 to about $10^6$ units of the IFN-γ.

9. A method for treating and/or preventing HTLV-1-related diseases, comprising
administering the agent of claim 1 to a subject suffering from an HTLV-1-related disease induced by HTLV-1 (human T-cell lymphotropic virus type 1).

10. The method of claim 9, wherein said HTLV-1-related disease is a member selected from the group consisting of adult T-cell leukemia (ATL), Sjögren syndrome, chronic rheumatoid arthritis, systemic lupus erythematosus (SLE), uveitis, and immunopathies.

11. The method of claim 9, wherein said agent is administered to said subject at a dose of one to $1 \times 10^4$ units/adult/day/kg of the body weight.

12. The method of claim 9, wherein said agent is administered to said subject at a dose frequency of 1–4 shots/day or 1–7 shots/week over one week to one year.

* * * * *